United States Patent [19]

Scholl

[11] Patent Number: 5,013,838

[45] Date of Patent: May 7, 1991

[54] POLYISOCYANATES CONTAINING ISOCYANURATE GROUPS AND A PROCESS FOR THEIR PRODUCTION

[75] Inventor: Hans-Joachim Scholl, Cologne, Fed. Rep. of Germany

[73] Assignee: Bayer Aktiengesellschaft, Bayerwerk, Fed. Rep. of Germany

[21] Appl. No.: 467,822

[22] Filed: Jan. 19, 1990

[30] Foreign Application Priority Data

Jan. 25, 1989 [DE] Fed. Rep. of Germany ....... 3902078

[51] Int. Cl.$^5$ ................... C07D 211/40; C08G 18/08; C08K 5/34
[52] U.S. Cl. .................. 544/193; 544/222; 528/48; 528/51; 524/101
[58] Field of Search ................... 544/222, 193

[56] References Cited

U.S. PATENT DOCUMENTS 3,748,329 7/1973 Liebsch et al. ............... 260/244

FOREIGN PATENT DOCUMENTS 1129173 6/1986 Japan ................... 544/221

OTHER PUBLICATIONS

Polyurethanes, Chem. & Tech., Saunders and Frisch, 1962, p. 94.

*Primary Examiner*—Mary C. Lee
*Assistant Examiner*—J. Richter
*Attorney, Agent, or Firm*—Joseph C. Gil; Thomas W. Roy

[57] ABSTRACT

The present invention relates to a process for the production of an isocyanurate group-containing polyisocyanate by (a) partially reacting the isocyanate groups of an organic diisocyanate containing aliphatically and/or cycloaliphatically bound isocyanate groups in the presence of an ammonium or phosphonium fluoride trimerization catalyst,
(b) introducing carbon dioxide into the reaction mixture at least periodically during the reaction and
(c) terminating the reaction at the desired degree of conversion.

The present invention also relates to the isocyanurate group-containing polyisocyanates obtained in accordance with this process.

24 Claims, No Drawings

POLYISOCYANATES CONTAINING ISOCYANURATE GROUPS AND A PROCESS FOR THEIR PRODUCTION

BACKGROUND OF THE INVENTION

1. Field of the Invention

This invention relates to a new process for the production of polyisocyanates containing isocyanurate groups in the presence of a trimerization catalyst and carbon dioxide and to the polyisocyanates obtained by this process.

2. Background of the Invention

The products obtained by the process according to the invention are generally mixtures which, in addition to isocyanurate polyisocyanates having the idealized formula (II), contain oxadiazinetrione diisocyanates having the idealized formula (I) and iminooxadiazinedione triisocyanates corresponding to formula (III):

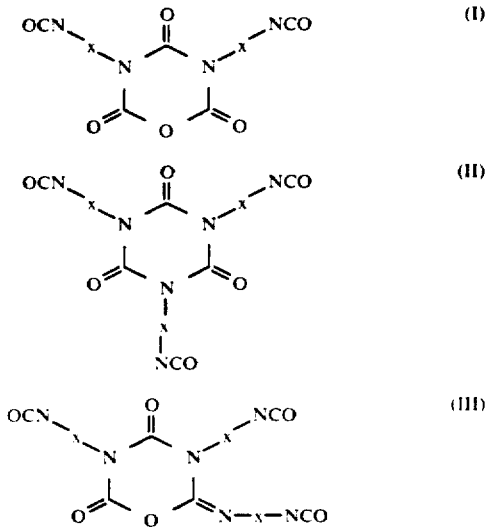

In these formulas, x is the hydrocarbon radical of the (cyclo)aliphatic diisocyanate used for the production of the modified polyisocyanates. In addition to the triisocyanates and diisocyanates corresponding to the above general formulae, the end products of the process according to the invention may also contain higher homologs having more than one heterocyclic ring of the type mentioned per molecule.

The process for the production of such polyisocyanate mixtures is new. It is true that there are several known processes for the trimerization of organic isocyanates using strong organic bases in particular as catalysts (J. H.. Saunders and K. C. Frisch, Polyurethanes, Chemistry and Technology, pages 94 et seq, 1962). When organic diisocyanates are used and when the trimerization reaction is terminated before all of the isocyanate groups of the starting diisocyanate have reacted, isocyanurate polyisocyanates are obtained which are valuable starting materials for the production of polyurethanes, in particular as the polyisocyanate component in polyurethane coating compositions. The combination of this trimerization reaction with the production of the oxadiazinetrione polyisocyanates described in DE-AS 1 670 666, i.e., the production of polyisocyanate mixtures corresponding to the end products of the process according to the invention, has not previously been described. This is not surprising because, on the one hand, carbon dioxide, an acid anhydride, hinders the base-catalyzed trimerization reaction and, on the other hand, carbon dioxide has to be present in excess in the process according to DE-AS 1 670 666 to avoid the formation of troublesome secondary products which cause an unwanted increase in viscosity.

It has now surprisingly been found that it is possible in accordance with the process of the present invention, which is described in detail hereinafter, to advantageously combine both modification reactions in such a way as to obtain modified isocyanurate polyisocyanates whose composition may be varied. The polyisocyanates are distinguished by a number of advantageous properties such as colorlessness, low viscosity and high compatibility with polyhydroxyl compounds commonly used with isocyanurate polyisocyanates.

SUMMARY OF THE INVENTION

The present invention relates to a process for the production of an isocyanurate group-containing polyisocyanate by (a) partially reacting the isocyanate groups of an organic diisocyanate containing aliphatically and/or cycloaliphatically bound isocyanate groups in the presence of an ammonium or phosphonium fluoride trimerization catalyst, (b) introducing carbon dioxide into the reaction mixture at least periodically during the reaction and (c) terminating the reaction at the desired degree of conversion.

The present invention also relates to the isocyanurate group-containing polyisocyanates obtained in accordance with this process.

DETAILED DESCRIPTION OF THE INVENTION

The use of quaternary ammonium or phosphonium fluorides as catalysts is critical to the process according to the invention. Any quaternary ammonium or phosphonium fluorides are suitable. The substituents at the nitrogen or phosphorus atom may be alkyl, aryl or aralkyl groups or mixtures thereof. Quaternary fluorides based on heterocyclic amines are also suitable. Preferred catalysts include compounds corresponding to the formula

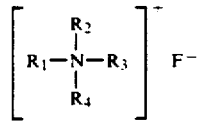

wherein $R_1$, $R_2$, $R_3$ and $R_4$ may be the same or different and represent alkyl groups containing 1 to 18, preferably 1 to 10 carbon atoms (one of the substituents may also be an aralkyl radical containing 7 to 15 carbon atoms), the sum of the carbon atoms in the four substituents preferably being 10 to 40; or the substituents $R_1$ and $R_2$ and optionally the substituents $R_3$ and $R_4$ together with the nitrogen atom may form a ring preferably containing 6 ring atoms and, optionally, additional hetero atoms.

Other preferred catalysts are, in particular, compounds corresponding to the formula in the preceding paragraph wherein $R_1$, $R_2$ and $R_3$ may be the same or different and represent alkyl radicals containing from 1 to 18, preferably 1 to 4 carbon atoms and more preferably methyl groups, and

R₄ represents a benzyl radical.

Suitable or preferred catalysts include tetramethyl ammonium fluoride, tetraethyl ammonium fluoride, tetra-n-propyl ammonium fluoride, tetra-n-butyl ammonium fluoride, N-methyl-N,N,N-trialkyl ammonium fluoride containing $C_{8-10}$ alkyl radicals, N,N,N-trimethyl-N-cyclohexyl ammonium fluoride, N,N,N-trimethyl-N-benzyl ammonium fluoride, N,N,N-triethyl-N-benzyl ammonium fluoride, N,N,N-trimethyl-N-phenyl ammonium fluoride, N,N,N-trimethyl-N-stearyl ammonium fluoride, N,N'-dimethyl triethylene diamine difluoride and N-methyl triethylene diamine monofluoride. Mixtures of these catalysts may also be used.

N-methyl-N,N,N-trialkyl ammonium fluoride containing $C_{8-10}$ alkyl radicals, N,N,N-tetra-n-butyl ammonium fluoride and N,N,N-trimethyl-N-benzyl ammonium fluoride are particularly preferred.

Suitable phosphonium fluorides, which are generally less preferred in comparison with the ammonium fluorides, include those corresponding to the above formula with the exception that phosphorus is present in place of nitrogen. Examples include tetramethyl phosphonium fluoride, tetraethyl phosphonium fluoride or tetra-n-butyl phosphonium fluoride.

The catalysts may be obtained, for example, by reacting (a) alkali fluorides, preferably sodium or potassium fluoride, more preferably potassium fluoride, with (b) quaternary ammonium or phosphonium salts of acids except hydrofluoric acid, preferably strong mineral acids and more preferably hydrochloric or hydrobromic acid, the reaction preferably taking place in an alcoholic reaction medium.

Quaternary ammonium or phosphonium salts suitable for the reaction include those corresponding to the formula

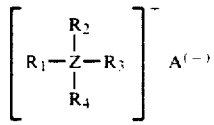

wherein

Z is nitrogen or phosphorus, $R_1$, $R_2$, $R_3$ and $R_4$ have the meanings and preferred meanings defined above and $A^{(-)}$ is the anion of a strong mineral acid except for hydrofluoric acid, preferably a chloride or bromide ion.

Typical examples of suitable starting materials (b) are the quaternary ammonium chlorides or bromides corresponding to the quaternary fluorides mentioned by way of example above or, less preferably, the phosphonium salts corresponding to those ammonium salts.

The catalysts are prepared, for example, by dissolving or suspending the alkali fluoride (a) in alcohols, such as methanol or ethanol, and then preferably adding an equimolar quantity of ammonium or phosphonium salt (b) with stirring. However, the quantities of (a) and (b) may be to 50 mole % more or less then the equivalent quantity. Neither the temperature nor the stirring time is critical. The components are normally stirred for about 20 to 60 minutes at room temperature and the ratio of alkali fluoride to alcohol is generally about 0.1 moles to 100-400 g alcohol.

In one embodiment for their production the catalysts are "absorbed" onto support materials (heterogeneous catalyst). In accordance with this method, the mixture of alkali fluoride and alcohol, preferably separated from insoluble constituents, is thoroughly stirred with the proposed support material and the alcohol is subsequently removed, for example under vacuum. Suitable support materials include silica gels, aluminum oxides and zeolites. Silica gels are preferred. The quantity of support material is selected so that there are about 0.05 to 5 mMol $F^-$, preferably about 0.1 to 2 mMol $F^-$ per g support material.

The catalyst system freed from insoluble constituents may also be used as a homogeneous catalyst after removal of the alcohol by dilution in solvents. Suitable solvents include 2-ethylhexane-1,3-diol, acetonitrile or dimethyl formamide. The quantity of solvent is selected so that there are about 5 0.005 to 0.5 mMol $F^-$ and preferably about 0.01 to 0.1 mMol $F^-$ per g solution.

The statement made in the foregoing that the ammonium fluorides are preferred over the phosphonium fluorides also applies to the catalysts produced by these methods.

The quantity of catalyst used in the process according to the invention depends upon the starting diisocyanate and on the type of catalyst (catalyst dissolved in solvent or absorbed on support material). While the particular quantity of catalyst required is best determined in a preliminary test, it is generally about 0.05 to 0.3 mMol $F^-$/mol diisocyanate in the case of homogeneous catalysis and about 1 to 1 mMol $F^-$/mol diisocyanate in the case of heterogeneous catalysis. However, with this type of catalyst on support materials, it is also possible to use larger quantities because the reaction can be stopped when required by filtration.

In certain cases, it may be advisable to support the catalytic effect of the catalysts with a small quantity of co-catalytically active urethane groups. Co-catalysts may be obtained, for example, by adding a small quantity of an alcohol (for example about 0.01 to 1% by weight, based on the weight of the starting diisocyanate); the alcohols added immediately react with the starting diisocyanate present in excess to form urethane groups. Suitable alcohols include methanol, ethanol, ethylene glycol or 2-ethylhexane-1,3-diol. The alcohols may be added with or before the primary catalyst.

Starting diisocyanates which are suitable for the process according to the invention include any organic diisocyanates containing aliphatically and/or cycloaliphatically bound isocyanate groups and having a molecular weight of 140 to 300 or mixtures of these diisocyanates. Examples include 1,4-diisocyanatobutane, 1,6-diisocyanatohexane (HDI), 1,5-diisocyanato-2-methyl pentane, 1,6-diisocyanato-2.2,4-trimethyl hexane, 1,12-diisocyanatododecane, 1,3-diisocyanatocyclobutane, 1,3- and/or 1,4-diisocyanatocyclohexane. 3,3'-dimethyl-4,4,'-diisocyanatodicyclohexyl methane, 4,4'-diisocyanatodicyclohexyl methane and 1-isocyanato3,3,5-trimethyl-5-isocyanatomethyl cyclohexane. The particularly preferred starting diisocyanate is 1,6-diisocyanatohexane (HDI).

The process according to the invention may be carried out in the absence of solvents or in the presence of inert solvents and diluents. Suitable inert solvents include apolar solvents (such as toluene, xylene or higher aromatic hydrocarbons), polar solvents (such as esters and ketones) and mixtures of such solvents.

In addition to the use of the catalysts mentioned by way of example, the presence of carbon dioxide during the process according to the invention is critical to the invention. The presence of carbon dioxide may be achieved by the periodic introduction of gaseous carbon dioxide into the reaction mixture during the process according to the invention. However, the process according to the invention is preferably carried out with continuous introduction of a carbon dioxide stream so that the reaction mixture is permanently saturated with carbon dioxide and excess carbon dioxide escapes from the reaction mixture.

The process according to the invention is generally carried out at a temperature of about 10 to 150° C., preferably about 20 to 100° C. The optimum reaction temperature depends upon the desired ratio of oxadiazinetrione (I) to isocyanurate (II). When using the same starting diisocyanate, a uniform introduction of $CO_2$ and the same catalyst, an increase in temperature results in an increase in the amount of isocyanurate group component (II). This tendency is further increased by reducing the addition of $CO_2$. By contrast, the iminooxadiazinedione component (III) remains small in size. Thus, the ratio of (I) to (II) within the claimed temperature range may be determined by a simple preliminary test. In general, about 0.01 to 10 oxadiazinetrione rings are present for every isocyanurate ring in the end products of the process according to the invention as shown by $^{13}C$-NMR spectroscopic analyses.

The reaction according to the invention is generally terminated at a conversion (conversion = percentage of isocyanate groups reacted, based on the total quantity of isocyanate groups present in the starting diisocyanate) of about 10 to 70%. The progress of the reaction may be followed, for example, by continuous determination of the refractive index or the NCO content.

When the process according to the invention is carried out in the absence of a solvent, optionally with subsequent removal of excess starting diisocyanate, for example in a thin-layer evaporator, the conversion is generally about 10 to 40%. When the process according to the invention is carried out in the presence of solvents without subsequent removal of unreacted starting isocyanate, the conversion is generally about 50 to 70%.

The manner in which the reaction is terminated depends upon the type of catalyst used. In the case of homogeneous catalysts, the reaction may be terminated by suitable catalyst poisons such as organic acids or acid chlorides which deactivate the catalysts. Examples include sulfonic acids (such as benzene or toluene sulfonic acid and their chlorides) or acidic esters of phosphorous acid or phosphoric acid (such as dibutyl phosphite, dibutyl phosphate or di-(2-ethylhexyl)-phosphate. These deactivators, which react chemically with and deactivate the catalysts, are generally added to the reaction mixture in a quantity at least equivalent to the catalyst. However, since the catalysts are partly deactivated during the reaction, it is often sufficient to add a subequivalent quantity of a deactivator, based on the quantity of catalyst added.

The trimerization reaction may also be terminated by the addition of substances which bind the catalyst by adsorption, including silica gels or fuller's earth, and which have to be subsequently removed, for example by filtration.

In the case of heterogeneous catalysts, the reaction may be terminated as previously mentioned by removal of the heterogeneous catalyst.

The end products of the process according to the invention may be freed from excess unreacted starting diisocyanates in known manner, for example by thin-layer distillation or extraction, particularly when the process according to the invention is carried out in the absence of solvents. Isocyanurate polyisocyanates containing less than 2% by weight, preferably less than 0.5% by weight of monomeric starting isocyanates may be obtained.

Excess starting diisocyanates are preferably removed in cases where the end products of the process are used as the isocyanate component in polyurethane coating compositions. Prior to their use, the end products of the process according to the invention may be modified, for example by the introduction of urethane, urea, biuret or allophanate groups.

The end products of the process according to the invention may also be used without the removal of excess starting isocyanates, for example for the production of polyurethane foams.

The end products of the process according to the invention may be blocked in known manner with suitable blocking agents for isocyanate groups such as phenol, ε-caprolactam, malonic acid diethyl ester or acetoacetic acid ethyl ester.

The end products of the process according to the invention or their derivatives as obtained by the blocking reaction are valuable starting materials for the production of polyurethane plastics by the isocyanate polyaddition process. They are particularly suitable as the isocyanate component in polyurethane coating compositions, particularly in two-component polyurethane paints. Coatings are prepared by reacting this isocyanate component with compounds containing at least two isocyanate-reactive groups, preferably hydroxyl groups.

The invention is illustrated by the following examples in which percentages are by weight, unless otherwise indicated.

EXAMPLES (A) Production of Catalysts in Solution

Example 1

16 g Aliquat 336[(1)] dissolved in 60 g ethanol were added with stirring at room temperature to 2.3 g potassium fluoride in 50 g ethanol. After 60 minutes, insoluble constituents were removed by filtration, 150 g 2-ethyl-hexane-1,3-diol were added to the filtrate and the ethanol was removed under vacuum. The catalyst solution had the following properties:

$F^-$: 0.21 mmol/g
$Cl^-$: 0.01 mmol/g

Example 2

2.9 g potassium fluoride in 70 g ethanol were reacted with stirring at room temperature with a solution of 7.4 g benzyl trimethyl ammonium chloride in 40 g ethanol. After 30 minutes, insoluble constituents were removed by filtration, 300 g 2-ethylhexane-1,3-diol were added to the filtrate and the ethanol was removed under vacuum.

$F^-$: 0.11 mmol/g
$Cl^-$: 0.02 mmol/g

Example 3

2% by weight benzyl trimethyl ammonium fluoride (Fluka GmbH) in 2-ethylhexane-1,3-diol:

$F^-$: 0.11 mmol/g (1) commercial quaternary ammonium chloride (Fluka GmbH) consisting essentially of N-methyl-N,N,N-trialkyl ammonium chloride containing $C_{8-10}$ alkyl groups (B) Production of Catalysts on Support Materials

Example 4

A solution of 81 g of the quaternary ammonium chloride used in Example 1 in 150 g ethanol was added at room temperature to 11.6 g potassium fluoride in 250 g ethanol. After 60 minutes, insoluble constituents were removed by filtration and the filtrate was stirred with 200 g Kieselgel 60 (Merck silica gel, 70-230 mesh, ASTM). After stirring for 60 minutes, the ethanol was removed under vacuum. A free-flowing catalyst system having the following properties was obtained:

$F^-$: 0.58 mmol/g
$Cl^-$: 0.03 mmol/g

Example 5

6.2 g potassium fluoride in 200 g ethanol were stirred at room temperature with a solution of 19.7 g benzyl trimethyl ammonium chloride in 100 g ethanol. After 20 minutes, insoluble constituents were removed by filtration and the filtrate was stirred with 200 g Kieselgel 60 (Merck silica gel, 70-230 mesh, ASTM). After stirring for 60 minutes, the ethanol was removed under vacuum. A free-flowing catalyst system having the following properties was obtained:

$F^-$: 0.42 mmol/g
$Cl^-$: 0.04 mmol/g (C) Process According to the Invention

Example 6

840 g (5 moles) HDI were heated to 40° C. while a stream of carbon dioxide was passed through the reaction vessel. The carbon dioxide stream was gauged in such a way that a slight excess of carbon dioxide continuously escaped from the reaction vessel through a bubble counter. 3 g of the catalyst of Example 1 were added dropwise with stirring at 40° C. while more carbon dioxide was introduced. Another 1 g of catalyst was added after 1 hour and a further 0.5 g were added after 2 hours. A refractive index $n^{23}_D$ of 1.4606 was reached after a total stirring time of 8 hours at 40° C. The reaction was terminated by the addition of 0.2 g phosphoric acid dibutyl ester and 10 g dried fuller's earth was added to the solution. This mixture was stirred for 30 minutes and then filtered. The filtrate was freed from excess HDI to a residual content of 0.1% HDI by thin-layer distillation ("short-path evaporator") at 120°C./0.1 mbar. A clear, colorless polyisocyanate having the following properties was obtained:

Yield: 168 g (20%)
NCO content: 22.2%
Viscosity 24° C.: 1700 mPa.s
Composition according to $^{13}$C-NMR (mole %): oxadiazinetrione (I): 68%; isocyanurate (II): 26%; iminooxadiazinedione (III): 6%.

Example 7

The procedure was the same as in Example 6 except that the reaction temperature was 60° C. and the quantity of catalyst was reduced (2 g, 0.5 g, 0.2 g). A refractive index of $n^{23}_D$ of 1.4630 was reached after 6 hours at 60° C. Working up in accordance with Example 6 provided a clear, colorless polyisocyanate having the following properties:

Yield: 205 g (24.5%)
NCO content: 22.1%
Viscosity 24° C.: 1600 mPa.s
Composition according to $^{13}$C-NMR (mole %): (I): 40%; (II): 45%; (III): 15%.

Example 8

The procedure was the same as in Example 6, except that the reaction temperature was 80° C. and the catalyst was added once in a quantity of 2 g. A refractive index $n^{23}_D$ of 1.4619 was reached after 3.5 hours. After working up, a clear, colorless polyisocyanate having the following properties was obtained:

Yield: 180 g (21.5%)
NCO content: 23.0%
Viscosity 24° C.: 1200 mPa.s
Composition according to $^{13}$C-NMR (mole %):(I): 20%; (II): 58%; (III): 18%.

Example 9

The procedure was the same as in Example 6, except that the reaction temperature was 100 C and the quantity of catalyst was reduced (1.5 g, 0.2 g, 0.1 g). A refractive index $n^{23}_D$ of 1.4604 was reached after 5 hours. After working up, a clear, colorless polyisocyanate having the following properties was obtained:

Yield: 154 g (18.4%)
NCO content: 23.5%
Viscosity 24° C.: 1000 mPa.s
Composition according to $^{13}$C-NMR (mole %):(I): 14%; (II): 63%; (III): 18%.

Example 10

840 g (5 moles) HDI were heated to 80° C. while a stream of carbon dioxide was passed through the reaction vessel. The carbon dioxide stream was gauged in such a way that a slight excess of carbon dioxide continuously escaped from the reaction vessel through a bubble counter. 2 g of the catalyst of Example 4 were then added with stirring at 80° C. Another 0.5 g catalyst were added after 2 hours and a further 0.5 g were added after another hour. A refractive index $n^{23}_D$ of 1.4620 was reached after a total stirring time of 5 hours. The heterogeneous catalyst was isolated by filtration and 10 g dried fuller's earth were added to the filtrate with stirring, but without heating, followed by stirring for 30 minutes and filtration.

The filtrate was freed from excess HDI to a residual HDI content of 0.1% by thin-layer distillation ("short-path s evaporator") at 120°C./0.1 mbar. A clear, colorless polyisocyanate having the following properties was obtained:

Yield: 170 g (21%);
NCO content: 21.6%
Viscosity 24° C.: 1600 mPa.s
Composition according to $^{13}$C-NMR (mole %): Oxadiazinetrione (I): 4%; isocyanurate (II): 95%

Example 11

As in Example 10, 1 g 2-ethylhexane-1,3-diol and 1.4 g of the catalyst of Example 4 were added at 80° C. Another 0.6 g catalyst was added after a stirring time of 3 hours at 80° C. A refractive index of $n^{23}_D$ of 1.4620 was reached after a total stirring time of 6 hours at 80° C. The heterogeneous catalyst was isolated by filtration and 10 g dried fuller's earth were added to the filtrate with stirring, but without heating, followed by stirring for 30 minutes and filtration.

The filtrate was freed from excess HDI to a residual HDI content of 0.1% by thin-layer distillation ("short-path evaporator") at 120°C./0.1 mbar. A clear, colorless polyisocyanate having the following properties was obtained:

Yield: 172 g (21.9%)
NCO content: 23.3%
Viscosity 24° C.: 1500 mPa.s
Composition according to $^{13}$C-NMR (mole %): Oxadiazinetrione (I): 3%; isocyanurate (II): 97%.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of an isocyanurate group-containing polyisocyanate which comprises
   (a) partially reacting the isocyanate groups of an organic diisocyanate containing aliphatically and/or cycloaliphatically bound isocyanate groups in the presence of an ammonium or phosphonium fluoride trimerization catalyst,
   (b) introducing carbon dioxide into the reaction mixture at least periodically during the reaction and
   (c) terminating the reaction at the desired degree of conversion.

2. The process of claim 1 which comprises removing unreacted organic diisocyanate by thin-layer distillation after termination of the reaction.

3. The process of claim 1 wherein said quaternary ammonium or phosphonium fluoride trimerization catalyst is obtained by reacting an alkali fluoride with a quaternary ammonium or phosphonium salt of an acid other than hydrofluoric acid.

4. The process of claim 2 wherein said quaternary ammonium or phosphonium fluoride trimerization catalyst is obtained by reacting an alkali fluoride with a quaternary ammonium or phosphonium salt of an acid other than hydrofluoric acid.

5. The process of claim 1 wherein said quaternary ammonium or phosphonium fluoride trimerization catalyst is obtained by reacting sodium or potassium fluoride in an alcoholic reaction medium with an ammonium or phosphonium salt corresponding to the formula

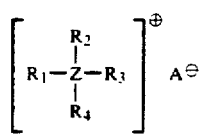

wherein
Z is nitrogen or phosphorus,
$R_1$, $R_2$, $R_3$ and $R_4$ may be the same or different and represent $C_{1-18}$ alkyl groups, one of the substituents may represent a $C_{7-15}$ araliphatic radical and the total number of carbon atoms in the four substituents is 10 to 40 and
$A^{\ominus}$ is the anion of a strong mineral acid except hydrofluoric acid.

6. The process of claim 2 wherein said quaternary ammonium or phosphonium fluoride trimerization catalyst is obtained by reacting sodium or potassium fluoride in an alcoholic reaction medium with an ammonium or phosphonium salt corresponding to the formula

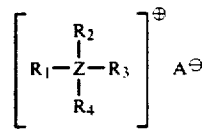

wherein
Z is nitrogen or phosphorus,
$R_1$, $R_2$, $R_3$ and $R_4$ may be the same or different and represent $C_{1-18}$ alkyl groups, one of the substituents may represent a $C_{7-15}$ araliphatic radical and the total number of carbon atoms in the four substituents is 10 to 40 and
$A^{\ominus}$ is the anion of a strong mineral acid except hydrofluoric acid.

7. The process of claim 1 wherein said organic diisocyanate comprises 1,6-diisocyanatohexane.

8. The process of claim 2 wherein said organic diisocyanate comprises 1,6-diisocyanatohexane.

9. The process of claim 4 wherein said organic diisocyanate comprises 1,6-diisocyanatohexane.

10. The process of claim 6 wherein said organic diisocyanate comprises 1,6-diisocyanatohexane.

11. A polyisocyanate mixture containing isocyanurate and oxadiazinetrione rings in a ratio of 0.01 to 10 oxadiazinetrione rings for each isocyanurate ring which is prepared by a process which comprises
   (a) partially reacting the isocyanate groups of an organic diisocyanate containing aliphatically and/or cycloaliphatically bound isocyanate groups in the presence of an ammonium or phosphonium fluoride trimerization catalyst,
   (b) introducing carbon dioxide into the reaction mixture at least periodically during the reaction and
   (c) terminating the reaction at the desired degree of conversion.

12. The polyisocyanate of claim 11 which comprises removing unreacted organic diisocyanate by thin-layer distillation after termination of the reaction.

13. The polyisocyanate of claim 11 wherein said quaternary ammonium or phosphonium fluoride trimerization catalyst is obtained by reacting an alkali fluoride with a quaternary ammonium or phosphonium salt of an acid other than hydrofluoric acid.

14. The polyisocyanate of claim 12 wherein said quaternary ammonium or phosphonium fluoride trimerization catalyst is obtained by reacting an alkali fluoride with a quaternary ammonium or phosphonium salt of an acid other than hydrofluoric acid.

15. The polyisocyanate of claim 11 wherein said quaternary ammonium or phosphonium fluoride trimerization catalyst is obtained by reacting sodium or potassium fluoride in an alcoholic reaction medium with an ammonium or phosphonium salt corresponding to the formula

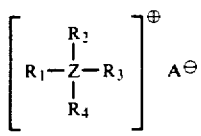

wherein
Z is nitrogen or phosphorus,
$R_1$, $R_2$, $R_3$ and $R_4$ may be the same or different and represent $C_{7-18}$ alkyl groups, one of the substituents may represent a $C_{7-15}$ araliphatic radical and the total number of carbon atoms in the four substituents is 10 to 40 and
$A^\ominus$ is the anion of a strong mineral acid except hydrofluoric acid.

16. The polyisocyanate of claim 12 wherein said quaternary ammonium or phosphonium fluoride trimerization catalyst is obtained by reacting sodium or potassium fluoride in an alcoholic reaction medium with an ammonium or phosphonium salt corresponding to the formula

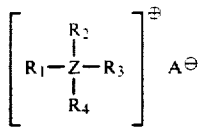

wherein
Z is nitrogen or phosphorus,
$R_1$, $R_2$, $R_3$ and $R_4$ may be the same or different and represent $C_{1-18}$ alkyl groups, one of the substituents may represent a $C_{7-15}$ araliphatic radical and the total number of carbon atoms in the four substituents is 10 to 40 and
$A^\ominus$ is the anion of a strong mineral acid except hydrofluoric acid.

17. The polyisocyanate of claim 11 wherein said organic diisocyanate comprises 1,6-diisocyanatohexane.

18. The polyisocyanate of claim 12 wherein said organic diisocyanate comprises 1,6-diisocyanatohexane.

19. The polyisocyanate of claim 14 wherein said organic diisocyanate comprises 1,6-diisocyanatohexane.

20. The polyisocyanate of claim 16 wherein said organic diisocyanate comprises 1,6-diisocyanatohexane.

21. The polyisocyanate mixture of claim 11 wherein the mixture contains at least 3 mole percent of compounds containing oxadiazinetrione rings.

22. The polyisocyanate mixture of claim 12 wherein the mixture contains at least 3 mole percent of compounds containing oxadiazinetrione rings.

23. The polyisocyanate mixture of claim 17 wherein the mixture contains at least 3 mole percent of compounds containing oxadiazinetrione rings.

24. The polyisocyanate mixture of claim 18 wherein the mixture contains at least 3 mole percent of compounds containing oxadiazinetrione rings.

* * * * *

UNITED STATES PATENT AND TRADEMARK OFFICE
CERTIFICATE OF CORRECTION

PATENT NO. : 5,013,838
DATED : May 7, 1991
INVENTOR(S) : Hans-Joachim Scholl

It is certified that error appears in the above-indentified patent and that said Letters Patent is hereby corrected as shown below:

IN THE CLAIMS:

In Claim 14, at column 10, line 61, delete "cf" and insert --of--.

In Claim 15, at column 11, line 11, delete "$C_{7-18}$" and insert --$C_{1-18}$--.

Signed and Sealed this

Tenth Day of December, 1996

Attest:

BRUCE LEHMAN

*Attesting Officer*    *Commissioner of Patents and Trademarks*